United States Patent [19]

Redburn

[11] Patent Number: 5,013,540

[45] Date of Patent: May 7, 1991

[54] USING NMDA RECEPTOR ANTAGONISTS TO REDUCE DAMAGE DUE TO LASER TREATMENT

[75] Inventor: Dianna A. Redburn, Houston, Tex.

[73] Assignee: Board of Regents, The University of Texas System, Houston, Tex.

[21] Appl. No.: 444,725

[22] Filed: Nov. 30, 1989

[51] Int. Cl.$^5$ .................. A61K 49/00; A61K 31/44
[52] U.S. Cl. ..................... 424/10; 514/289; 514/922
[58] Field of Search ............ 424/10; 604/21, 22; 514/922, 289

[56] References Cited

U.S. PATENT DOCUMENTS 4,806,543  2/1989  Choi ........................... 514/464

OTHER PUBLICATIONS

Tortella. Tips 10:501-507 (Dec. 1989).
Goldberg. Neuroscience letters 80:11-15 (1987).
Monyer, Brian Research 446:144-148 (1988).
Choi, Journal of Pharmacology and Experimental Therapeutics 242(2):713-720 (1987).
Leavens, Cancer Bulletin 41:237-240 (1989).
Jacques, Cancer Bulletin 41:211-218 (1989).
Thomsen, Cancer Bulletin 41:203-210 (1989).
Von Eschenbach, Cancer Bulletin 41:201-202 (1989).
Choi, Brain Research 403:333-336 (1987).
Kleinermanns, K. et al. "Laser Chemistry—What is its Current Status?" Angew. Chem. Int. Ed. Engl. 26:38-58 (1987).

*Primary Examiner*—Glennon H. Hollrah
*Assistant Examiner*—Gary E. Hollinden
*Attorney, Agent, or Firm*—Arnold, White & Durkee

[57] ABSTRACT

A method is disclosed for preventing the spread of damage in neuronal tissue that has been selectively burned by surgical laser treatment. Administration of an NMDA receptor blocker, such as dextrorphan. in conjunction with the laser treatment permits the site of the laser burn to be confined more precisely to the desired area, and prevents the spread of damage to surrounding tissue that would normally occur in the days after the laser treatment.

12 Claims, No Drawings

USING NMDA RECEPTOR ANTAGONISTS TO REDUCE DAMAGE DUE TO LASER TREATMENT

FIELD OF THE INVENTION

The present invention relates to laser surgery in living neuronal tissue such as the retina, and more specifically to methods of reducing the damaging effects of laser treatment to such tissue.

BACKGROUND OF THE INVENTION

Laser surgery is a technique which is finding increasing use in a number of situations. Physicians today routinely use lasers in a number of specialized procedures, including reshaping the cornea of the eye and ablating disfiguring skin lesions such as port wine stains. Lasers are used for delicate surgical microdissection in the brain, but are also capable of blasting apart obstructing kidney and gallbladder stones, removing calcified arteriosclerotic plaque from obstructed blood vessels, and destroying tumors.

Another major surgical use of lasers is in retinal photocoagulation, which is used to treat diabetic patients suffering from diabetic retinopathy. There are approximately 7,000,000 diabetics in the United States today (approximately 2.8% of the population), and of these, approximately 700,000 have retinal complications. Diabetic hyperglycemia is often the triggering factor for these complications. It leads to retinal hypoxia which in turn stimulates the production of the vasogenic factor which causes neovascularization. About one tenth of the patients having such retinal complications are candidates for laser photocoagulation treatment. The general purpose of such treatment is to destroy the areas of neovascularization, and to preserve other areas of the retina.

Retinal photocoagulation can be divided into several categories of treatment. Local photocoagulation treatment consists of confluent laser burns applied to the specific neovascularization and a 500 $\mu$ area around it. Focal photocoagulation treatment consists of single laser burns applied to isolated vascular lesions which are near the fovea and thus threaten central vision. Panretinal photocoagulation consists of 1500 laser burns which literally ablate the majority of peripheral retina tissue, but are intended to leave the fovea and parafoveal region intact. Thus, the hypoxic peripheral retina is sacrificed along with a large portion of the peripheral visual field and night vision in order to decrease the production of vasogenic factor and hopefully save the fovea and central vision.

Another use of laser photocoagulation is to repair retinal tears and retinal detachment. The neural retina is composed of a thin layer of neurons which hangs together as a translucent sheet and overlays supportive tissue of the eye ball. The retina is physically attached to the other structures of the eye in two regions: the area of the optic disc near the center of the retina, and in the area of the ora serrata which forms the peripheral edge of the retina. Under normal conditions, these points of attachment serve to keep the retina flattened snugly against the back of the eyeball. In cases of trauma to the eye, intraretinal bleeding (such as occurs with diabetes), processes associated with "normal" aging, and in some cases where etiology is unknown, the retina does not maintain its flattened position. The retina can become too tightly stretched and small tears in the retinal tissue can occur; the retinal surface can become ruffled, or small blobs can form, causing the retina to become detached from the underlying tissue. Left unattended, small areas of disruption can lead to much larger areas of detachment. Areas of detached retina do not maintain normal function and may actually undergo necrosis. These areas are routinely treated with lasers in order to produce photocoagulated tissue which will act to re-bond the retina to underlying tissue. Vision in this region is lost, but further retinal detachment is prevented.

Laser surgery in general has a number of advantages, such as permitting operations with smaller exposure, more precise control of what tissue is eliminated, reduced blood loss during surgery, reduced postoperative edema, shorter operative time, and potentially reduced operative mortality and morbidity and increased longevity. However, laser surgery also has some disadvantageous side effects For example, when lasers are used to treat neuronal tissue such as the retina, the damage resulting from the laser burn usually spreads into surrounding healthy tissue. The size of lesions caused by laser burns in retinal tissue increases in the days immediately following the laser treatment. There are several mechanisms for the damage caused by lasers.

Photothermal effects are caused by transformation of absorbed light energy into heat. Depending on the amount of heat generated, tissues are (1) destroyed by vaporization and/or combustion, (2) carbonized, or (3) coagulated. A second category, photochemical effects, result from photoactivation of certain exogenous photosensitizers selectively sequestered in various tissues, such as cancerous growths, to produce toxic substances that destroy the tissue or lesion. The actual mechanism of action is not well understood; however, in some cases it involves the light activation of photosensitizers which interact with molecular oxygen to form singlet oxygen, a strong oxidant, which in turn causes oxidation of vital cell constituents. A third category consists of photoacoustic mechanical effects which involve the rapid heating and expansion of the target tissue. This creates an explosive shock wave that may disrupt, fragment, or ablate cells, organelles and extracellular matrix in the absence of overt thermal or chemical reactions.

The present invention stems from the belief that, in addition to the above-listed mechanisms, glutamate may play a role in causing damage to tissue surrounding a laser burn.

Glutamate is a highly abundant compound in the nervous system, where it serves a number of diverse functions. As an amino acid, it serves as one of the building blocks for the synthesis of various proteins; as a metabolite in the tricarboxylic acid cycle, it is important in energy metabolism; it is the principal excitatory neurotransmitter used in the central nervous system; and it is used to a lesser extent as a transmitter in the peripheral nervous system. When glutamate is released from intracellular stores into the extracellular space, it has strong depolarizing actions on most neurons with which it comes in contact. Several cellular systems operate to restrict or "buffer" the normal level of glutamate found extracellularly. High affinity uptake systems for glutamate are found on glutamatergic neurons and they serve to recycle the released glutamate. Similar uptake systems are located on glial cells which accumulate and degrade glutamate into its inactive metabolite, glutamine. Virtually any cellular insult or injury in the nervous system, including a laser burn, can lead either directly or indirectly to a loss of the integrity of the intracellular storage pools of glutamate, a breakdown in glutamate uptake activity and an interruption of glutamate metabolism. The net result is an increase in extracellular glutamate, massive depolarization or excitation of surrounding neurons and, in many cases, widespread cell death. Thus glutamate excitotoxicity may mediate cell death associated with a wide variety of primary neuronal injuries and may represent one of the final common pathways for cell death in the brain and other parts of the nervous system.

The actions of extracellular glutamate are believed to be brought about by the binding of glutamate to one of four different types of membrane receptors which are found on most neurons. One specific type of glutamate receptor is thought to be a quiescent or silent receptor during normal housekeeping types of neuronal activity, but may be called into play or activated during specific neuronal processing events such as learning or memory recall. This receptor is named after the glutamate analogue for which it has highest affinity, N-methyl-D-aspartate (NMDA). Magnesium normally binds the NMDA receptor, maintaining it in an inactive state. Two signals lead to activation of the receptor, namely a change in membrane potential (depolarization) or an increase in calcium. These changes occur during repetitious neuronal firing which may associated with the types of neuronal activity expressed during a learning trial. The displacement of magnesium from the NMDA receptor allows glutamate to bind to the receptor and open a high conductance ionophore, leading to additional influx of sodium and potassium, and further depolarization. Thus the initial activation of a neuron by glutamate through non-NMDA receptors or by some other excitatory neurotransmitter will make the cell more sensitive to any subsequent exposure to extracellular glutamate.

This unique property of the NMDA type of glutamate receptor is believed to make it a likely candidate for participation in glutamate induced cell death. Glutamate, released in response to some initial cellular injury, would make surrounding neurons even more susceptible to glutamate depolarization through NMDA receptors, with a massive influx of sodium and potassium, leading to ionic imbalances, eventual cell death and release of more glutamate. Because of the domino effect, the initial site of injury would be increased many fold because of spreading secondary damage caused by glutamate interaction with NMDA receptors.

As noted above, laser surgery has a number of benefits, but it also has the disadvantage when used on neuronal tissue that healthy tissue surrounding the area of the burn is usually damaged soon after the laser treatment. The present invention provides means of reducing this damage, and therefore makes the laser treatment even more desireable.

SUMMARY OF THE INVENTION

The present invention relates to a method of reducing the damaging effects of laser treatment on neuronal tissue, which includes the step of administering to a living subject an effective amount of an NMDA receptor blocker in conjunction with laser treatment of neuronal tissue in that subject. The NMDA receptor blocker can be administered to the subject prior to the laser treatment, concurrently with it, or both prior to and concurrently. One group of NMDA receptor blockers that can be used in the present invention is the opioid compounds, and dextrorphan and pharmaceutically acceptable salts thereof are specific examples.

In a specific embodiment of the present invention, the NMDA receptor blocker is administered to the subject at a dosage rate of 10–25 mg/kg of body weight given as a bolus, followed by an additional 10–25 mg/kg administered over a period of approximately two hours. The dosage rate should be selected so that it will not cause very heavy sedation or breathing problems.

The present invention should be useful as an adjunct to laser treatment of various types to neuronal tissue such as, for example, the retina or the brain. When used as an adjunct to laser eye surgery, the present invention should block the secondary damage and permit the lesion to be confined to the original targeted area. This will prevent the laser-induced lesion from spreading to the foveal area of the retina, the area that is used most by humans for visual tasks.

Further, the use of the present invention with respect to retinal tissue provides a useful tool for evaluating the effectiveness of NMDA receptor blockers in general. The highly reproducible nature of laser burns in retinal tissue, the relatively greater accessibility of retinal tissue compared to other neuronal tissue, and the highly laminar histological structure of the retina permit precise quantitative evaluation of the damage caused by a given laser burn in the presence of a given potential NMDA receptor blocker. For example, fundus photographs of the retina can be used to determine the morphological size of the lesion resulting from a laser burn. As another alternative, blind spots in the peripheral vision could be mapped out and the blockage of functional loss by NMDA receptor blockers could thereby be determined.

DETAILED DESCRIPTION OF SPECIFIC EMBODIMENTS

One compound which is useful in the method of the present invention is dextrorphan, the O-demethylated metabolite of dextromethorphan. The monohydrochloride salt of dextrorphan (Ro 16794/706) is freely soluble in water. Dextrorphan is a noncompetitive antagonist of the central nervous system glutamate receptor, particularly the NMDA receptor subtype. It has been shown to possess NMDA receptor antagonist properties in both in vivo and in vitro models. It freely crosses the blood-brain barrier after systemic administration.

Dextrorphan (obtained from Hoffman LaRoche) was used to test the present invention with respect to laser burns in the retinas of rabbits. Prior to beginning the tests themselves, background testing was performed to determine the tolerance levels of experimental animals when given the drug intravenously. Testing was done in the range of 10–25 mg/kg given as a bolus, followed by a maintained delivery of an additional 10–25 mg/kg over a two hour period. It was found that the 25 mg/kg bolus followed plus 25 mg/kg over the subsequent two hours was tolerated by the rabbits, but higher doses caused very heavy sedation and breathing problems.

Testing of the present invention was then performed by applying a series of laser burns in the rabbits before dextrorphan treatment and another series of burns in the same rabbits four hours after the dextrorphan treatment as described above. Six animals were tested; some in both eyes and some in only one eye. The animals were sacrificed three days later. Retinal tissue was fixed and serially sectioned in 15 μ sections throughout the entire burn area. A total of 20 burns were applied to each eye in groups of two rows, with each row occupying the tissue present in fifty or more sequential slides. This means that over 1500 individual quantitative and qualitative measurements were made of these 120 burns in six animals.

The results showed that at all intensities of laser treatment applied (80–600 milliwatts; 10–1000 μ spot sizes), the size of the laser-damaged area of the retina and the underlying choroid tissue was smaller in the row of burns applied after dextrorphan treatment when compared to the row of burns in the same eye made before treatment. The protection produced by the dextrorphan treatment amounted to about a 35% reduction in the diameter of the damaged area, which represents a reduction of more than 50% in the total area of damage.

Quantitative assessment of the protective effects suggests that (1) dextrorphan reduces the amount of swollen tissue, (2) protection may occur not only in the neural retina but also in the vascular and epithelial tissue underlying the neural retina, (3) the area around the edges of a laser burn may show the greatest protection, and (4) dispersion of pigment granules from the pigmented epithelium may be decreased. This last finding is especially important in the retina because dispersed pigment granules can significantly interfere with vision.

Other drugs which are believed to NMDA receptor antagonists and therefore useful in the present invention include ketamine, a commonly used anesthetic, the numbered compound MK801 (Merck, Sharpe & Dohme)

NMDA receptor blockers in accordance with the present invention can be administered in formulations which comprise the NMDA receptor blocker itself with a pharmaceutically acceptable carrier or diluent. The NMDA receptor blockers, or formulations thereof, can be administered to the subject in a number of ways. For example, the administration could be by intravenous, intraarterial, intramuscular, intralymphatic, intraperitoneal, subcutaneous, intrapleural, or intrathecal injection, or by topical application or oral dosage. In the case of uses of the present invention on retinal tissue, it is preferred to administer the NMDA receptor blocker specifically to the eye, so that it will not reach the brain, thereby preventing possible undesirable side effects. This could be done by administering the substance in the form of eyedrops or a time-release implant which would be placed under the eyelid or to the side of the eye.

The preceding is not intended to be an exhaustive list of all possible embodiments of the present invention. Instead, it is intended to provide examples of specific embodiments of the invention. Persons skilled in this field will recognize that modifications could be made to the examples in this patent which would remain within the scope of the invention.

I claim:

1. A method of reducing the damaging effects of laser treatment on neuronal tissue, including the step of administering to a living subject an effective amount of a NMDA receptor blocker compound in conjunction with laser treatment of neuronal tissue in that subject.

2. The method of claim 1, where the NMDA receptor blocker compound is an opioid compound.

3. The method of claim 1, where the NMDA receptor blocker compound is selected from the group consisting of dextrorphan and pharmaceutically acceptable salts thereof.

4. The method of claim 1, where the NMDA receptor blocker compound is administered to the subject prior to the laser treatment.

5. The method of claim 1, where the NMDA receptor blocker compound is administered to the subject approximately concurrently with the laser treatment.

6. The method of claim 1, where the NMDA receptor blocker compound is administered to the subject both prior to and approximately concurrently with the laser treatment.

7. A method of reducing the damaging effects of laser treatment on retinal tissue, including the step of administering to a living subject an effective amount of an NMDA receptor blocker compound in conjunction with laser treatment of retinal tissue in that subject.

8. The method of claim 7, where the NMDA receptor blocker compound is an opioid compound.

9. The method of claim 7, where the NMDA receptor blocker compound is administered to the subject prior to the laser treatment.

10. The method of claim 7, where the NMDA receptor blocker compound is administered to the subject approximately concurrently with the laser treatment.

11. The method of claim 7, where the NMDA receptor blocker is administered to the subject both prior to and approximately concurrently with the laser treatment.

12. The method of claim 7, where the NMDA receptor blocker compound is selected from the group consisting of dextrorphan and pharmaceutically acceptable salts thereof.

* * * * *

UNITED STATES PATENT AND TRADEMARK OFFICE
CERTIFICATE OF CORRECTION

PATENT NO. : 5,013,540

DATED : 5/7/91

INVENTOR(S) : Dianna A. Redburn

It is certified that error appears in the above-identified patent and that said Letters Patent is hereby corrected as shown below:

At column 5, line 26, the word --be-- should appeare after "to".

At column 5, line 28, the word --and-- should appear after "anesthetic,".

Signed and Sealed this

Twenty-ninth Day of December, 1992

Attest:

DOUGLAS B. COMER

Attesting Officer

Acting Commissioner of Patents and Trademarks